(12) United States Patent
Berend et al.

(10) Patent No.: US 11,234,770 B2
(45) Date of Patent: Feb. 1, 2022

(54) FEMORAL MEDIAL CONDYLE SPHERICAL CENTER TRACKING

(71) Applicant: Biomet Manufacturing, LLC, Warsaw, IN (US)

(72) Inventors: Michael E. Berend, Indianapolis, IN (US); Pierre Couture, Montreal (CA)

(73) Assignee: Biomet Manufacturing, LLC, Warsaw, IN (US)

( * ) Notice: Subject to any disclaimer, the term of this patent is extended or adjusted under 35 U.S.C. 154(b) by 607 days.

(21) Appl. No.: 16/129,188

(22) Filed: Sep. 12, 2018

(65) Prior Publication Data

US 2019/0076198 A1 Mar. 14, 2019

Related U.S. Application Data

(60) Provisional application No. 62/557,392, filed on Sep. 12, 2017.

(51) Int. Cl.
*A61B 34/20* (2016.01)
*A61B 17/17* (2006.01)
(Continued)

(52) U.S. Cl.
CPC .......... *A61B 34/20* (2016.02); *A61B 17/1703* (2013.01); *A61B 17/1721* (2013.01); *A61B 17/1764* (2013.01); *A61B 34/30* (2016.02); *G06T 7/73* (2017.01); *G06T 7/74* (2017.01); *A61B 2034/2055* (2016.02); *A61B 2034/2057* (2016.02); *A61B 2034/2065* (2016.02);
(Continued)

(58) Field of Classification Search
CPC ..... A61B 34/20; A61B 17/17; A61B 17/1703; A61B 17/1721; A61B 17/1764; G06T 7/73; G06T 7/74
See application file for complete search history.

(56) References Cited

U.S. PATENT DOCUMENTS 8,512,346 B2    8/2013  Couture
2005/0096535 A1*  5/2005  de la Barrera ......... A61B 90/36
                                                600/424
(Continued)

OTHER PUBLICATIONS

"Oxford Partial Knee Microplasty Instrumentation Surgical Technique", Zimmer Biomet; 0297.2-US-en-REV1017, (2017), 56 pgs.
(Continued)

*Primary Examiner* — Christopher J Beccia
(74) *Attorney, Agent, or Firm* — Schwegman Lundberg & Woessner, P.A.

(57) ABSTRACT

Systems and methods for femoral medial condyle spherical center identification and tracking are described herein. Once the spherical center of the medial condyle is identified, the spherical center is tracked using a pin or internal reference. The spherical center may be used to provide a key kinematic motion reference, such as when the medial condyle is adjusted during a surgical procedure. The tracking may be used to provide optical tracking, inertial tracking, or other tracking. In contrast with surface-mounted optical trackers, the spherical center tracking is not lost during resection (e.g., removal) of a bone surface. Tracking the medial condyle spherical center may reduce or eliminate the need for a surface-mounted optical tracker or preoperative 3-D modeling or of the joint.

18 Claims, 10 Drawing Sheets

(51) Int. Cl.
  *G06T 7/73* (2017.01)
  *A61B 34/30* (2016.01)
  *G06T 19/00* (2011.01)

(52) U.S. Cl.
  CPC ............... *A61B 2034/2068* (2016.02); *A61B 2034/2074* (2016.02); *G06T 19/006* (2013.01); *G06T 2207/30008* (2013.01)

(56) References Cited

U.S. PATENT DOCUMENTS

2007/0066917 A1* 3/2007 Hodorek ............... A61B 34/20
  600/595
2017/0312031 A1  11/2017 Amanatullah et al.
2017/0312032 A1  11/2017 Amanatullah et al.

OTHER PUBLICATIONS

Eckhoff, Donald G, et al., "Three-Dimensional Mechanics, Kinematics, and Morphology of the Knee Viewed in Virtual Reality", The Journal of Bone & Joint Surgery, vol. 81, (Dec. 4, 2005), 71-80.
Iranpour, F., et al., "Patellar Tracking: Relationship with Distal Femoral Geometry", Poster No. 1983; 55th Annual Meeting of the Orthopaedic Research Society, (Feb. 2009), 1 pg.

\* cited by examiner

FEMORAL MEDIAL CONDYLE SPHERICAL CENTER TRACKING

CLAIM OF PRIORITY

This application claims the benefit of U.S. Provisional Patent Application Ser. No. 62/557,392, filed on Sep. 12, 2017, the benefit of priority of which is claimed hereby, and which is incorporated by reference herein in its entirety.

BACKGROUND

Advancements in surgical procedures have improved articular surgical procedures, such as knee replacement, hip arthroplasty, ligament repair, knee replacement, and other surgical procedures. As an example, the Oxford® Partial Knee provides an advanced meniscal arthroplasty, which may be used to treat the progression of anteromedial osteoarthritis and provide long-term symptom relief. Various surgical tools have improved surgical outcomes, however many of these surgical tools depend on manual placement of the surgical tool. Positive outcomes for patients in procedures using manual placement and control of surgical tools rely heavily on the skill and experience of the surgeon.

Navigated surgery addresses some of the deficiencies of manual placement and control of surgical tools. One solution includes mounting optical tracking pins, however these pinned optical trackers are invasive. Mounting optical trackers on an articular surface is one solution to the problem of invasive, pinned optical trackers, such as described in U.S. Pat. No. 8,512,346. However, even with articular surface mounted optical trackers, the optical reference tracker is lost once the articular surface cut is made. Further, while current techniques for navigated surgery provide some ability to perform mechanical alignment, they provide limited ability to perform kinematic alignment techniques.

DETAILED DESCRIPTION

Figure 1:
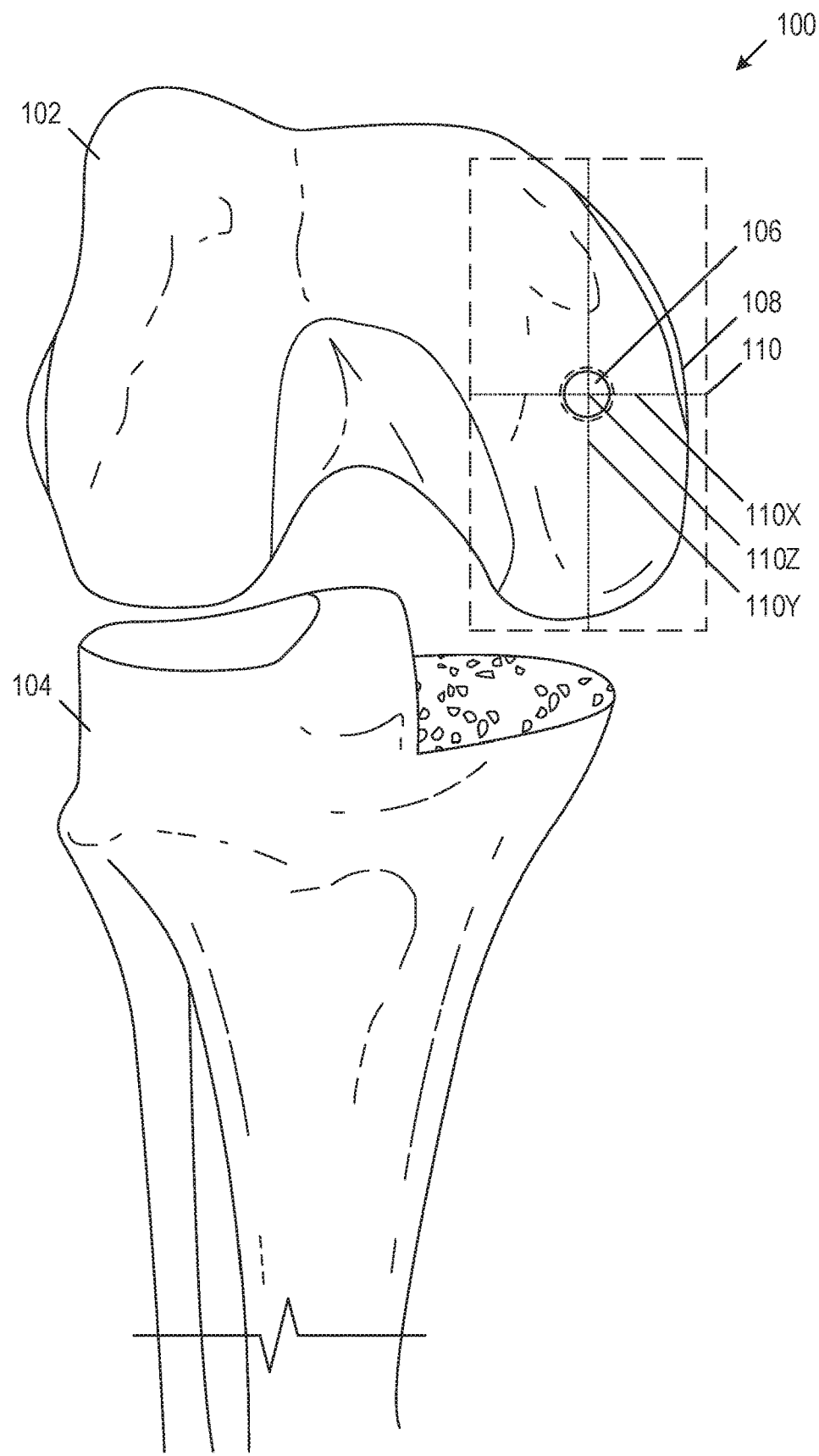
FIG. 1 illustrates a front view of medial condyle spherical center identification and tracking, in accordance with some embodiments.

Systems and methods for navigated knee surgery and for assessment and recreation of kinematic alignment are described herein. Navigated surgery using optical trackers may be improved by applying optical tracking based on the spherical center of the femoral medial condyle. The inventors have recognized, among other things, that it is beneficial to track anatomical elements and dynamically adjust a surgical procedure on the knee based on the location of the medial condyle spherical center. For example, in making resections for a total or partial knee arthroplasty, identifying the medial condyle spherical center and adjusting location and orientation of the resections based on tracking the spherical center may result in more accurate resections that assist in restoring the desire range of motion in the reconstructed knee joint. In an example, tracking information related to the medial condyle spherical center may be provided in real-time to a surgical robot programmed to perform or guide resections of the knee based on preoperative planning utilizing the medial condyle spherical center as a reference point. In general, the natural movement of the knee favors rotation around the medial condyle spherical center, both during and following the operation. Tracking anatomical elements (e.g., the tibia, the femur) based on the medial condyle spherical center therefore improves the effectiveness of using the patient's particular anatomy to guide the surgical procedures and improve surgical outcomes. Using a reference point below the surface of the target anatomy (e.g., the distal end of the femur) provides a stable reference that can be repeatedly used throughout the operation.

In the drawings, which are not necessarily drawn to scale, similar numerals may describe similar components in different views. Like numerals having different letter suffixes may represent different instances of similar components. The drawings illustrate generally, by way of example, but not by way of limitation, various embodiments discussed in the present document.

FIG. 1 illustrates a front view of medial condyle 100 with the spherical center 106 for identification and tracking, in accordance with some embodiments. Several surgical techniques rely on a mechanical positioning instrument to position a surgical instrument relative to the distal end of the femur 102 and the proximal end of the tibia 104. In accordance with techniques discussed herein, the surgical instrument may be positioned relative to the spherical center 106 of the femoral medial condyle 106. The spherical center 106 represents the origin (e.g., center point) of a sphere whose surface best matches the surface of the medial femoral condyle 108. The spherical center 106 may be determined preoperatively or intraoperatively, such as by using the techniques (e.g., workflows) described in FIGS. 3A-3C below. In various embodiments, the spherical center 106 is identified by mechanical surgical instruments (e.g., calipers, spoons), where the mechanical surgical instruments are operated by a surgeon or by a surgical robot. In an example, a caliper under the medial femoral condyle 108 is used to identify the location of the spherical center 106, and the caliper may be used in subsequent surgical procedure steps.

Once identified and marked with a tracker (e.g., optical tracker, inertial tracker), the spherical center 106 is used to provide guidance for various surgical procedures. In various embodiments, the spherical center 106 will be tracked as the anatomical reference point (e.g., anatomical landmark) during robotically assisted or navigated surgery. In an embodiment providing robotically assisted articular implant surgery (e.g., knee replacement), robotic technology may execute surgical navigation (e.g., mapping) based on the spherical center 106 to prepare the remaining bone for replacement, to position portions of the implant, or to perform other surgical procedures. For example, preoperative and intraoperative planning will reference the spherical center, such as when preparing the bone for resurfacing or executing resurfacing. In various embodiments, tracking of the spherical center 106 may be augmented by tracking using additional surgical landmarks (e.g., surgical tracking markers attached to adjacent anatomy). In another embodiment, augmented reality (AR) assisted surgery may be used to track the spherical center 106 or other known location and superimpose information on the location, such as a coordinate system 110. Coordinate system 110 may include a Cartesian coordinate system, such as an x-axis 110X, a y-axis 110Y, and a z-axis 110Z (projecting toward the viewer). In various examples, coordinate system 110 may be centered on the spherical center 106 or may be offset from the spherical center 106 to align with related landmarks or otherwise assist in tracking aspects of the surgical procedure.

Figure 2:
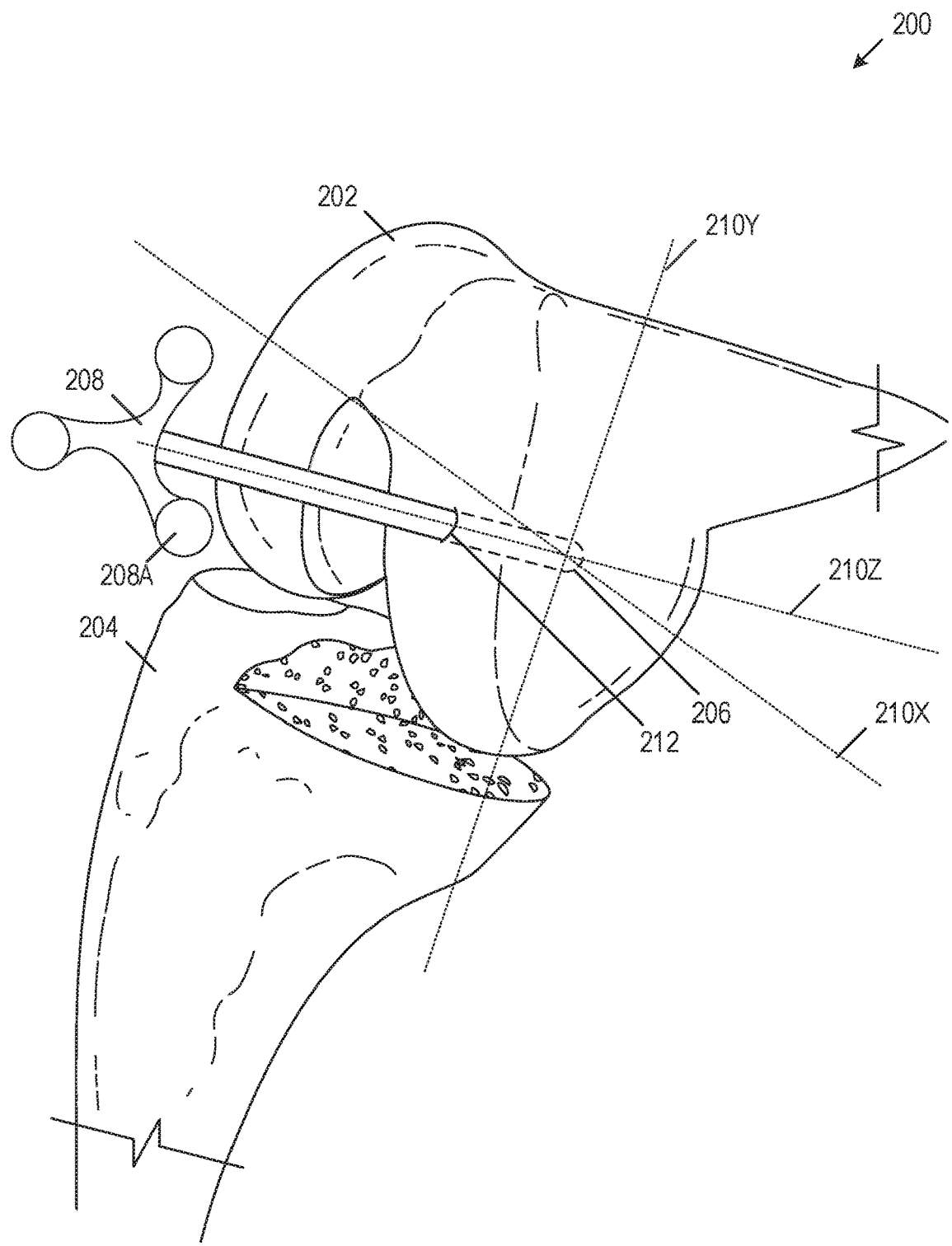
FIG. 2 illustrates a perspective view of medial condyle spherical center identification and tracking, in accordance with some embodiments.

FIG. 2 illustrates a perspective view of medial condyle spherical center identification and tracking 200, in accordance with some embodiments. FIG. 2 shows the spherical center 206 within the femoral head 202, and shows an example 3-axis coordinate system whose origin is superimposed on the spherical center 206, which includes an x-axis 210X, a y-axis 210Y, and a z-axis 210Z. FIG. 2 shows an example surgical tool 208 that may be used to insert a device to track the location of the spherical center 206, such as a spherical center optical tracking array 208A for optical navigation or a microelectromechanical system (MEMS) inertial pod for inertial navigation. For example, an optical tracker placed using surgical tool 208 may include sensors that may determine knee kinematics in relationship to the location of the femoral head and a tracker on the tibia, which may be used to determine knee kinematics for implant placement. Surgical tool 208 may include a structure that maintains the tracking array 208A in a predetermined orientation. For example, the rod of the surgical tool 208 may have a cross-section that can only be inserted in a particular orientation, such as a T-shaped cross-section, an isosceles triangle cross-section, an egg-shaped cross-section, or another orientation-specific cross-section. Surgical tool 208 may include a structure that stops upon reaching the spherical center 206, such as a rounded end. In other embodiments, the surgical tool 208 can include an additional post that can be inserted into an orientation bore adjacent to the bore extending to the spherical center 206. The orientation bore can include a different diameter (e.g., smaller bore) to assist in ensuring the surgical tool 208 is inserted with the proper orientation. As noted above, the bore holes in the medial condyle can be of sufficient depth to allow them to be used even after resections of the medial condyle performed as part of the knee arthroplasty procedure.

Once the spherical center 206 is identified, a hole 212 may be drilled along an axis 210A that is parallel or substantially parallel to the femur into the medial condyle spherical center 206. In an embodiment, a surgical operator may use an interactive display (e.g., touchscreen, screen and mouse, augmented reality display) to identify femoral landmarks relative to the spherical center 206, and a surgical robot may be used to drill the hole 212 based on the identified landmarks. In an embodiment, the drilled hole 212 may be used to secure an optical tracking pin or other physical internal tracking reference, providing the ability to track the spherical center 206. The drilled hole 212 may be used to provide a rigid fixation on the femur to ensure proper tracking. In an embodiment, a rigid tracker may be press-fit into the femur. In an embodiment, an optical tracker, such as an L-shaped optical tracker may be used to provide optical tracking while reducing or eliminating visual occlusion of the surgical site.

The spherical center 206 may be tracked to provide "true kinematic" analysis of the joint, which may provide important joint diagnostic information. For example, the use of true kinematic analysis provides the ability to characterize the kinematic envelope of the knee, such as through a physical analysis of the movement of the joint conducted by manipulating the femur and tibia (e.g., circumduction) while tracking the relative or absolute femur and tibia locations. The true kinematic analysis may also include using torque or force sensors while moving the tibia or femur through various ranges of motion and into various positions to understand stability, tension values, and other biomechanical information. The true kinematic characterization of the kinematic envelope of the knee described herein provides improved patient-specific information about the structure of the knee that is not provided by alternate joint analysis methodologies. For example, a surgical technique often referred to as "kinematics" does not include movement of the tibia or femur. Instead, the "kinematics" provides a simulated kinematic alignment based on using mechanical measurement tools and bony landmarks to estimate the post-operative knee structure or mechanical alignment (e.g., instrumentation). However, the simulated kinematic techniques provide estimations that are missing various important biomechanical limitations, such as the laxity of ligaments and other tissue that may be characterized properly through the true kinematic analysis. Because many knee joints undergoing surgery have at least some fibers intact, the movement of the tibia and femur during true kinematic analysis provides a reliable kinematic envelope that may be characterized by a surgical robot. In an example, the true kinematic analysis determines resection depth based on a measurement device inserted between the femur and tibia during various positions in flexion and extension of the tibia. The measurement device may add tension, and may include an adjustable spacer, a surgical spoon, or other surgical device.

The true kinematic analysis described herein also provides robotic surgical tool placement not provided by alternative surgical alignment techniques. For example, in contrast with the use of robotic navigation based on preoperative image capture and analysis, this true kinematic analysis provides the ability to characterize the kinematic envelope, using a robot to record information to determine the kinematic envelope characteristics, and then using the robotically determined kinematic envelope to execute cuts, to place cut guides, to place surgical tools and implants, or to perform other surgical techniques to recreate or improve the kinematic envelope.

In an embodiment, the spherical center 206 may be used to place a cut guide based on the location of the spherical center 206. In another embodiment, the spherical center 206 may be used to place a pin guide, insert pins, remove the pin guide, and place a cut guide based on the pin locations. The spherical center 206 may be used to provide a kinematic motion reference, such as when the medial condyle is adjusted during a surgical procedure. This merges established mechanical instrumentation methods with navigated and kinematically aligned methods via robotics. In contrast with surface-mounted optical trackers that are removed during resection (e.g., removal) of a bone surface, the use of an internal tracking reference secured by the drilled hole 212 enables spherical center 206 tracking during and following various surgical procedures. The drilled hole 212 may be used as a basis for physically locating various resection tools, such as a cut guide, a patient-specific instrument, a reference point, an anchoring point, or a landmark to be reassessed to verify a resecting procedure. Tracking the medial condyle spherical center 206 may eliminate the need for a surface-mounted optical tracker, and may reduce the need for preoperative 3-D modeling of the joint.

Identification of the spherical center 206 provides various advantages for knee surgeries. Using the spherical center 206, the femur may be prepared for partial knee replacement, such as by resection of femoral or tibial surfaces. Tracking the spherical center 206 may be used in total knee replacement for kinematic alignment (e.g., ligament referencing) to use soft tissue around the knee to direct robotically assisted surgery, which improves accuracy over landmark-based mechanical alignment. The location of the spherical center 206 may be used to transfer kinematic alignment or mechanical alignment information to another area, such as to the lateral condyle or a tracking frame attached to another area of the femur outside the surgical field. As explained more fully with respect to FIG. 5 below, a coordinate system based on the spherical center may be transferred 506 from the surgical tracking device to a robotic surgical device, and the coordinate system may be transferred 512 from the robotic surgical device back to the tracking device upon completing the surgical procedures. In an embodiment, a tracking frame attached to a secondary location may be utilized for navigation or robotic tracking and assistance in resection.

The use of the spherical center 206 within kinematic alignment and other surgical procedures may be used to improve various aspects of the surgical procedures, such as improving placement of surgical implants. For example, tracking the spherical center 206 may improve rotational alignment of the tibial component during total or partial knee replacement procedures. Tracking the spherical center 206 may be used to verifying one or more surgical procedure steps, such as verifying resection depth following a resection procedure. For example, in contrast with a condyle surface-mounted surgical landmark, the internal tracking of the spherical center 206 provides an anatomic landmark that is not lost due to cutting an articular surface. Additionally, some existing robotically assisted surgical techniques rely on MRI or CT scans, where the scans are programmed into the surgical robot, and where the robot executes mapping based on the preoperatively programmed scans and intraoperatively confirmed surgical landmarks. In contrast, the use of the spherical center 206 provides a surgical landmark that enables preoperative and intraoperative surgical planning without the need for an MRI or CT scan, thereby reducing time and cost associated with a procedure.

In addition to the coordinate system 210, the location of the spherical center 206 provides various advantages for augmented reality surgical procedures. An augmented reality (AR) device allows a user to view displayed virtual objects superimposed onto physical objects, such as viewing the 3-axis coordinate system 210 superimposed on the spherical center 206. AR devices typically include two displays (e.g., lenses, screens), such as one display for each eye of a user. Light is permitted to pass through the two displays such that aspects of the real environment are visible while also projecting light to make virtual elements visible to the user of the AR device.

An AR device includes an AR display that may be used to display a virtual component while allowing real objects to be viewed. In addition to the location of the spherical center 206, the virtual component may include measurements, angles, an identification of an impingement (e.g., a femoroacetabular impingement), or a potential impingement, a representation of an implant, a representation of patient anatomy, a range of motion plane or axis, or other virtual component. For example, alignment angles may be shown virtually on an image of a patient or on a virtually presented skeleton, for example overlaid on the patient, using the AR display.

Patient imaging may be performed (e.g., using a CT scan, an MRI, an X-ray, etc.) to create at least one patient image. In an example, two images may be used (e.g., two-dimensional images) to create a three-dimensional representation of an aspect of a patient's anatomy. The three-dimensional representation may be displayed virtually using an AR display. When displayed virtually, the three-dimensional representation may be manipulated or observed in the AR display (e.g., rotated, moved, zoomed-in, zoomed-out, virtually cut, etc.).

Two or more AR devices may be used in a coordinated manner, such as with a first AR device controlling one or more additional AR devices. Two or more AR devices may be used within a system with defined user roles. In an example, when activating an AR device, a user may select a role (e.g., patient, surgeon, nurse, or other clinician) and the AR device may display information relevant to that role. In another example, the AR display for a surgeon may include more information or more complex or technical information than the AR display for a patient, which may be simplified for ease of understanding. In another example, the surgical AR device may control what is viewed on the patient AR device.

Within an AR display environment, virtual aspects overlaid on the real environment may be represented as anchored or in a set position relative to one or more aspects of the real environment. For example, a virtual object may be configured to appear to be resting on a table. An AR system may present virtual aspects that are fixed to a real object without regard to a perspective of a viewer or viewers of the AR system. For example, the virtual object may exist in a room, visible to a viewer of the AR system within the room and not visible to a viewer of the AR system outside the room. The virtual object in the room may be displayed to the viewer outside the room when the viewer enters the room. In this example, the room may act as a real object that the virtual object is fixed to in the AR system.

An AR display of the spherical center 206 may include one or more screens, such as a single screen or two screens (e.g., one per eye of a user). The screens may allow light to pass through the screens such that aspects of the real environment are visible while displaying the virtual object. The virtual object may be made visible to a surgeon by projecting light. The virtual object may appear to have a degree of transparency or may be opaque (i.e., blocking aspects of the real environment).

An AR system may be viewable to one or more viewers, and may include differences among views available for the one or more viewers while retaining some aspects as universal among the views. For example, a heads-up display may change between two views while virtual objects may be fixed to a real object or area in both views. Aspects such as a color of an object, lighting, or other changes may be made among the views without changing a fixed position of at least one virtual object.

A user may see the virtual object presented in an AR system as opaque or as including some level of transparency. In an example, the user may interact with the virtual object, such as by moving the virtual object from a first position to a second position. For example, the user may move an object with his or her hand. This may be done in the AR system virtually by determining that the hand has moved into a position coincident or adjacent to the object and causing the object to move in response. One or more cameras may be used within the AR system, where the cameras may be mounted on an AR device, and where the cameras may be static or may be controlled to move.

Virtual aspects may include virtual representations of real world objects, or virtual aspects may include visual effects (e.g., lighting effects, etc.). The AR system may include rules to govern the behavior of virtual objects, such as subjecting a virtual object to gravity or friction, or may include other predefined rules that defy real world physical constraints (e.g., floating objects, perpetual motion, etc.). An AR device may include a camera on the AR device. The AR device camera may include an infrared camera, an infrared filter, a visible light filter, a plurality of cameras, a depth camera, etc. The AR device may project virtual items over a representation of a real environment, which may be viewed by a user. A surgeon may control a virtual object using the AR device, using a remote controller for the AR device, or by interacting with the virtual object (e.g., using a hand to "interact" with the virtual object or a gesture recognized by the camera of the AR device).

The AR device and the AR device may be part of a shared AR system. The shared AR system may allow the AR devices to view the same or similar content, to be in communication with each other, for one to control the other, or similar device-to-device communication. For example, the surgeon may control the AR device of the patient using the clinician's own AR device (e.g., using a remote, a gesture, a button on the AR device, etc.). In an example, the surgeon and the patient may select their respective roles when initiating one or more of the shared AR devices.

By assigning roles to the AR devices, the AR devices may automatically provide appropriate virtual objects to be displayed. For example, the surgeon may select the clinician role for the AR device. Once the clinician role is selected, the surgeon may be presented with a plurality of choices for display, such as diagnostic tools, viewing imaging of the patient, selecting a patient file, education information, or other choices. When the surgeon selects a choice, the AR device may display virtual objects or information corresponding to the choice. In an example, the AR device may automatically display virtual objects or information (which may correspond to the choice, to the clinician-displayed virtual objects or information, or may be derived from the choice or the clinician-displayed virtual objects or information) for view by the patient. For example, the surgeon may choose to view an image of a bone of the patient. The image may be previously obtained. The AR device may display, in response to the choice, a three-dimensional view of the bone, and for example, additional clinical information (e.g., technical data). The AR device may automatically display, in response to the choice a three-dimensional view of the bone without the additional clinical information or with basic educational information (e.g., labels for names of parts of the bone). In an example, the surgeon may manipulate the virtual representation of the bone (e.g., using a button or gesture to rotate or zoom the bone) and the changes to the bone may be automatically reflected in the AR device of the patient.

Figure 3:
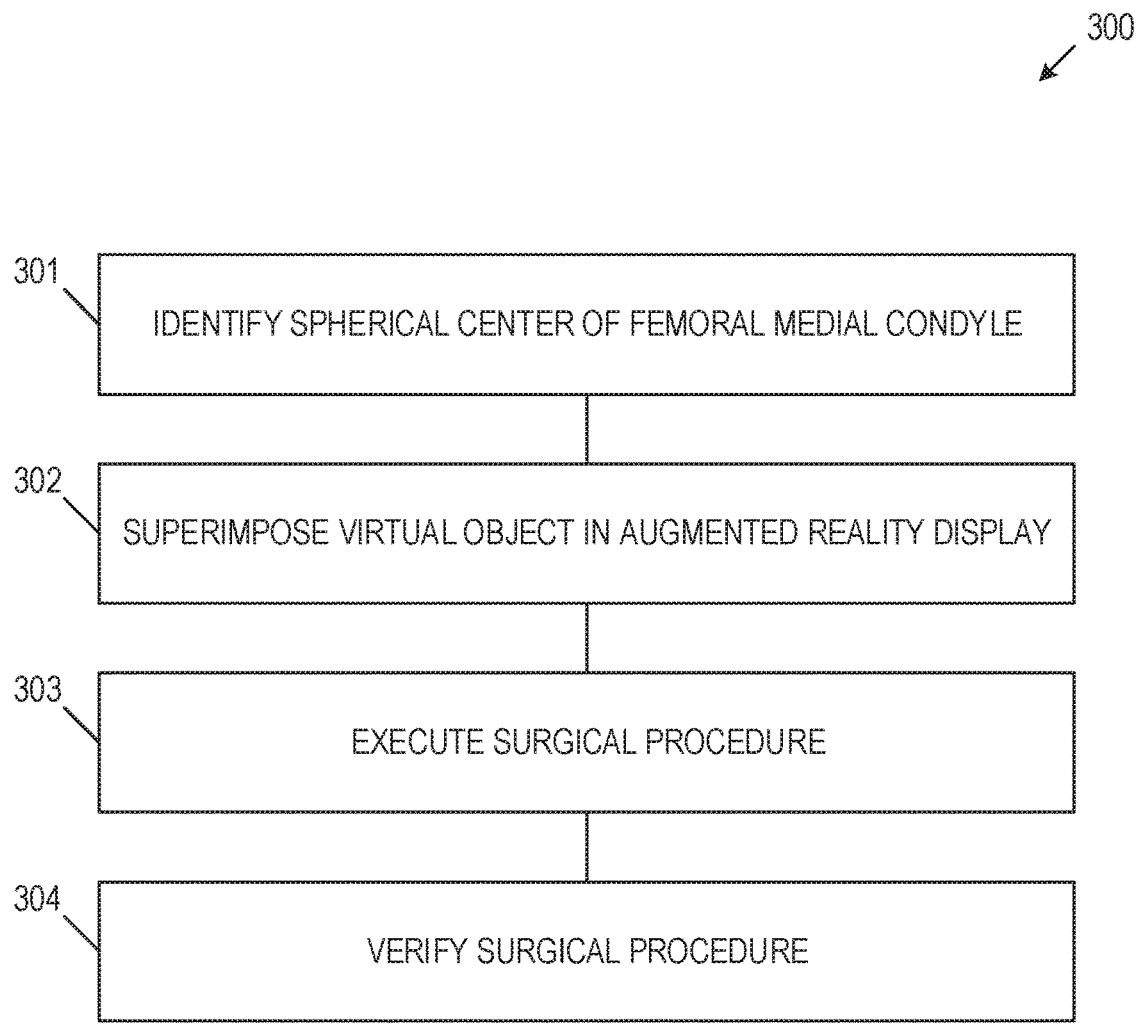
FIG. 3 illustrates a first technique for femoral medial condyle spherical center tracking, in accordance with some embodiments.

FIG. 3 illustrates a flow chart showing a first technique 300 for femoral medial condyle spherical center tracking, in accordance with some embodiments. Technique 301 includes identification 301 of the spherical center of the medial condyle. The spherical center may be identified preoperatively, such as using 3-D modeling of the joint. In an embodiment, the spherical center may be identified intraoperatively, reducing or eliminating the need for a surface-mounted optical tracker or preoperative 3-D modeling or of the joint. Identification 301 of the spherical center may include surgical attachment of a tracking device at or near the spherical center. Various technique for identification 301 of the spherical center are illustrated and described in FIGS. 3A-3C below, which provide detailed examples of various techniques 301A-301C for identifying the spherical center of the femoral medial condyle.

Technique 301 includes superimposing 302 an object within an augmented reality display. The object may be superimposed based on the location of the spherical center. The superimposed object may include a coordinate system, a surgical tool guide, textual information, or other information. Technique 301 includes executing 303 a surgical procedure. The surgical procedure may be executed by a surgical robot or by a surgeon using the known location of the spherical center.

Following the surgical procedure 303, one or more aspects of the surgical procedure may be verified 304. For example, executing 303 a surgical procedure may include resecting of an articular surface, and verification 304 of the surgical procedure may include determining whether a sufficient portion of the articular surface was excised. The verification 304 of the surgical procedure may be performed by superimposing a virtual map of the desired final articular surface structure onto a visual display of the articular surface, by performing articular surface measurements using the surgical robot, or through another tracked validation tool. In an embodiment, the depth of resection is determined by ligament balancing with feeler gauges, which is provided as feedback to the robotic system. This verification of resecting may be used during a partial knee replacement surgery or a total knee replacement surgery.

In an embodiment, the execution 303 of a surgical procedure or the verification 304 of the surgical procedure may include comparing a measured femoral medial condyle spherical center and radius against a determined femoral medial condyle spherical center and radius. In this embodiment, a tibial-femur gap is measured with a sensor when the knee is bent and when the knee is straightened to 20 degrees. Because of the spherical geometry of a healthy femoral medial condyle, the posterior condyle distance and joint line distance should be substantially equal or within a predetermined tolerance. Any difference will indicate how much of the femoral medial condyle should be resected during execution 303 of the surgical procedure to recreate the spherical geometry of the femoral medial condyle. Similarly, verification 304 of the surgical procedure may include verification that the posterior condyle distance and joint line distance are substantially equal or within a predetermined tolerance.

Figure 3A:
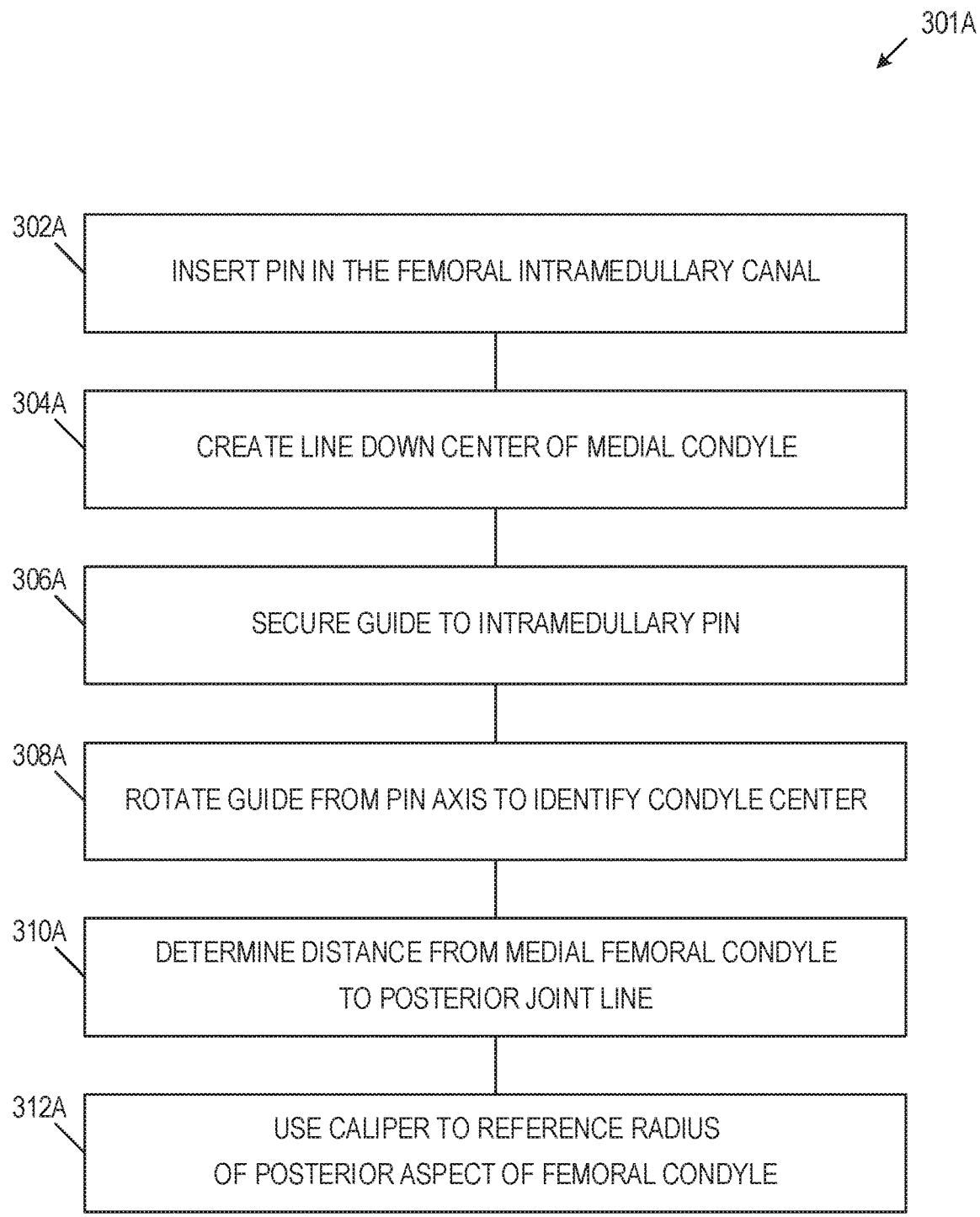
FIGS. 3A-3C illustrate techniques for femoral medial condyle spherical center identification, in accordance with some embodiments.
Figure 3B:
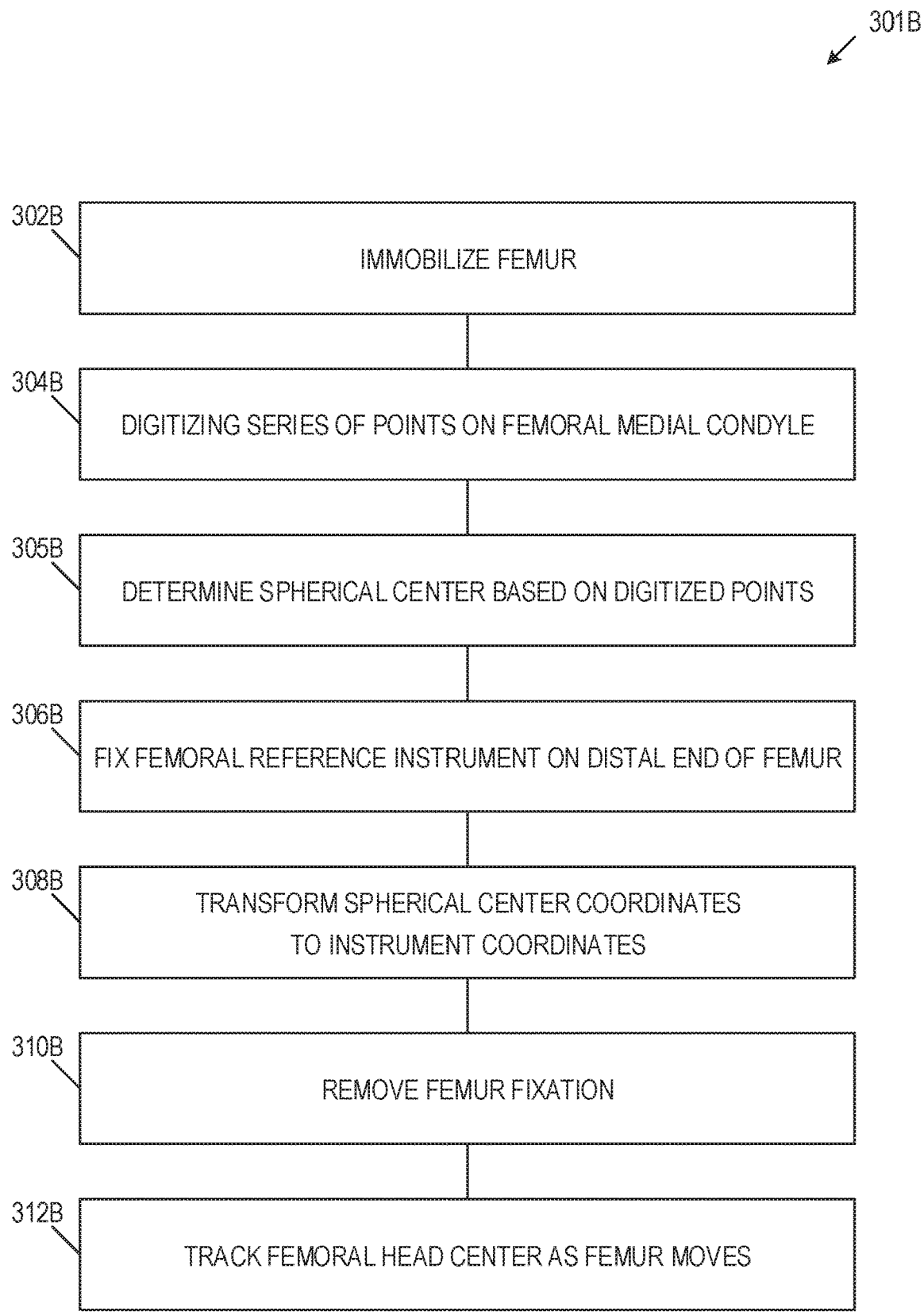
Figure 3C:
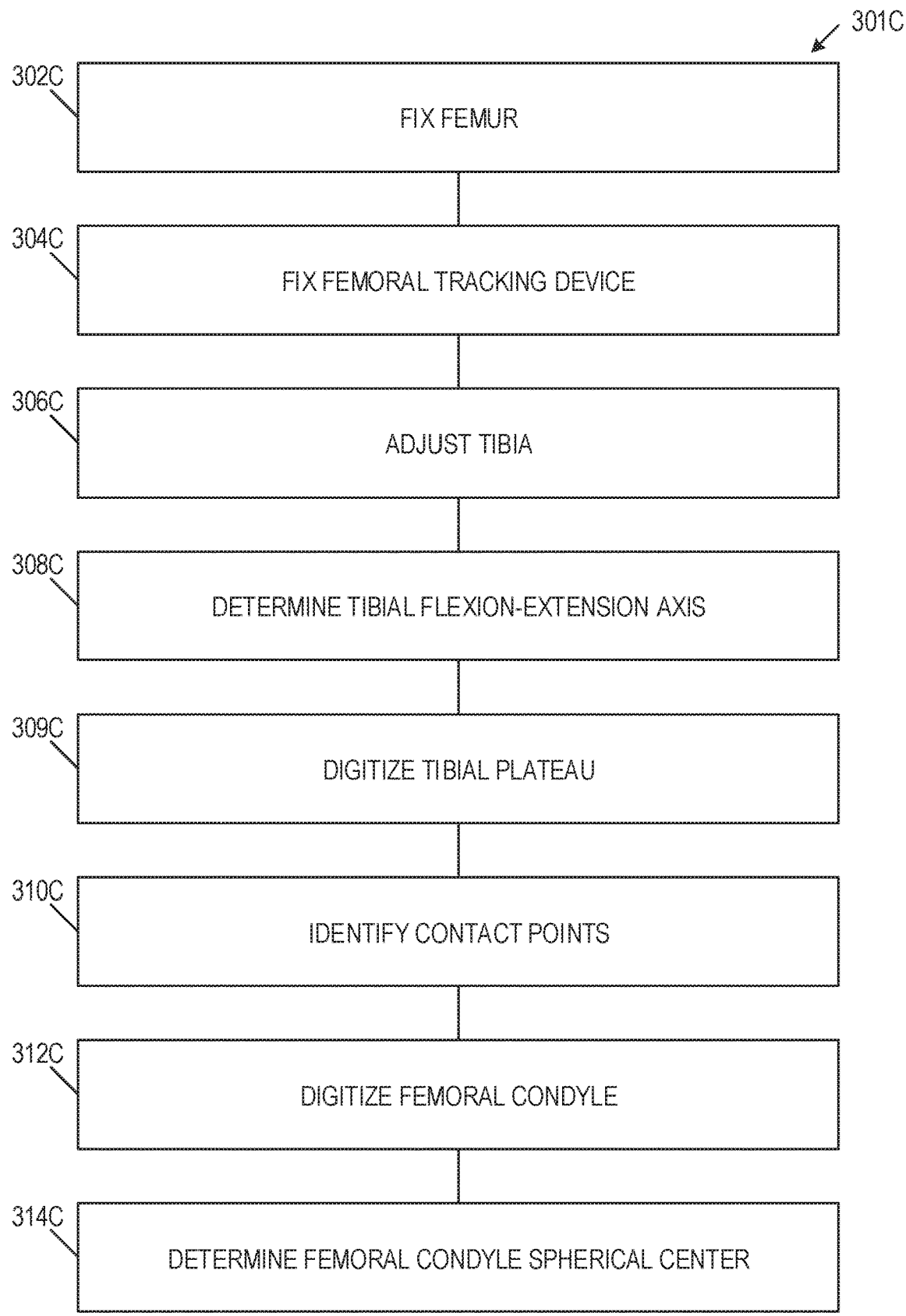

FIGS. 3A-3C illustrate techniques for identifying a femoral medial condyle spherical center, in accordance with some embodiments. A surgical procedure using the tracking methods discussed herein may begin with a manual location of the spherical center of the medial femoral condyle. FIG. 3A illustrates a technique 301A for manual identification of femoral medial condyle spherical center. In this example, technique 301A can include operations such as inserting a pin in the femoral intramedullary canal 302A, creating a line down the center of the medial femoral condyle 304A, securing a guide to the pin 306A, rotating the guide identify the center 308A, determining 310A the distance to the distal and posterior joint line, and verifying by referencing the radius of the posterior aspect of the femoral condyle 312A.

In this example, technique 301A may begin by inserting a pin in the femoral intramedullary canal 302A and creating a line down the center of the medial condyle 304A. At 306A, technique 301A can continue with a surgeon securing a guide to the intramedullary pin 306A, such as securing a drill guide or pin guide. At 308A, technique can continue with rotating the guide from the pin axis to identify the center of the medial condyle 308A. The guide may be used to identify the external location and depth of the spherical center of the medial condyle. Additional techniques may be used to identify or verify the location of the spherical center. For example, the spherical center may be identified or verified based on determining 310A the distance from the medial femoral condyle to the distal and posterior joint line. The spherical center may be identified or verified based on using a caliper to reference 312A the radius of the posterior aspect of the femoral condyle.

FIG. 3B illustrates a technique 301B for a first computer-assisted identification of femoral medial condyle spherical center. The spherical center of the medial femoral condyle may be located through various tracking or robotic procedures (e.g., workflows). In this example, technique 301B can include operations such as immobilizing the femur 302B, digitizing points on the femoral medial condyle 304B, determining the spherical center based on the digitized points 305B, fixing a femoral reference instrument on the femur 306B, transforming coordinates of the spherical center the femoral reference instrument coordinate system 308B, removing the femur fixation 310B, and tracking 312B the center of the femoral head. In this example, technique 301B begins by immobilizing the femur 302B, such as using an articulated arm or a leg-holder. Technique 301B can continue by digitizing a series of points on the femoral medial condyle 304B. Digitizing points on the surface of the femoral medial condyle can be done using an optically tracked pointer, or similar device. Using the digitized points, technique 301B can continue by determining the spherical center of the femoral medial condyle 305B. In this example, determining the spherical center can be done by fitting a sphere to the digitized points and locating the center of the fit sphere. In an alternative embodiment, the spherical center determination may include locating a mid-line of the medial femoral condyle, determining a mid-line plane using mechanical axis information, and fitting a circle to digitized points on the mid-line plane. Technique 301B can continue by fixing a femoral reference instrument (e.g., femoral bone tracker) on the distal end of the femur while the femur remains fixed, where the femoral reference instrument provides a tracking location that is fixed relative to the spherical center location. In certain examples, the femoral reference instrument is inserted into a bore hole drilled into the femoral medial condyle to locate a known end of the femoral reference instrument in close proximity to the spherical center. Technique 301B can transform coordinates of the spherical center of the femoral medial condyle to a coordinate system based on the femoral reference instrument location and orientation 308B, such as by using a tracking system (e.g., optical tracking system). Once the coordinate system is transformed, technique 301B can include removing the femur fixation 310B, which allows the femur to move. Technique 301B can then use the rigidly fixed femoral reference instrument to track the center of the femoral head as the femur moves 312B.

FIG. 3C illustrates a third technique 301C for computer-assisted identification of femoral medial condyle spherical center. In this example, technique 301C includes fixing the femur 302C, fixing a tracking device to the tibia 304C, adjusting the tibia 306C determine tibial flexion-extension axis 308C, digitizing the tibial plateau 309C, identifying contact points between the femur and tibia 310C, digitizing the femoral condyle 312C, and determining the femoral condyle spherical center 314C. In the technique 301C shown in FIG. 3C, the spherical center may be identified based on the kinematics of the knee, which may be determined based on a range of movement of the tibial plateau below the femur. A true kinematic analysis may be used to determine the flexion axis of the tibia (e.g., tibial flexion-extension axis, tibial flexion-extension plane). In an example true kinematic analysis, the flexion axis is determined, a surgical procedure is executed, and a surgical implant is positioned to recreate the flexion axis.

In this example, technique 301C begins with fixing the femur 302C, such as by securing the femur to a table. At 304C, technique 301C can continue by fixing a tracking device to a patient's tibia. For example, a tracking boot may be secured to a patient's tibia or foot. At 306C, technique 301C can continue by adjusting the tibia in flexion and extension. At 308C, technique 301C can continue by determining the tibial flexion-extension axis. For example, determining the tibial flexion-extension axis 308C includes determining multiple tracking points within a virtual coordinate system throughout tibial adjustment 306C, which may provide a rotation axis orientation and location within the virtual coordinate system. If the flexion determined in 308C becomes misaligned during surgery, the surgical robot may make minor modifications to guide soft tissue release. In another example, the system provides information regarding soft tissue balance to the surgeon, who can use the soft tissue information to perform soft tissue releases. For example, while robotic surgical navigation reduces or eliminates misalignment, the soft tissues may still become imbalanced. This soft tissue imbalance may be identified and corrected by the surgical robot, such as by identifying and performing soft tissue releases.

At 309C, technique 301C can continue by digitizing the tibial plateau. Using the tibial plateau and the tracking points, technique 301C can identify various contact points between the femur and tibia 310C in various positions. Technique 301C may use the tibial plateau and the femur-tibia contact points to digitize the femoral condyle 312C. At 314C, technique 301C uses the digitized femoral condyle to determine the femoral condyle spherical center 314C. In this example, the digitized points of the medial femoral condyle are used in a manner similar to that discussed above to identify the spherical center. A surgical robot may use the spherical center and tibial flexion-extension plane to provide precise placement of surgical tools or implants relative to that plane. By using one or more of these robotic or non-robotic methods to determine the spherical center of the medial femoral condyle, this spherical center location may be used to determine the placement of partial knee and total knee replacement components.

Figure 4:
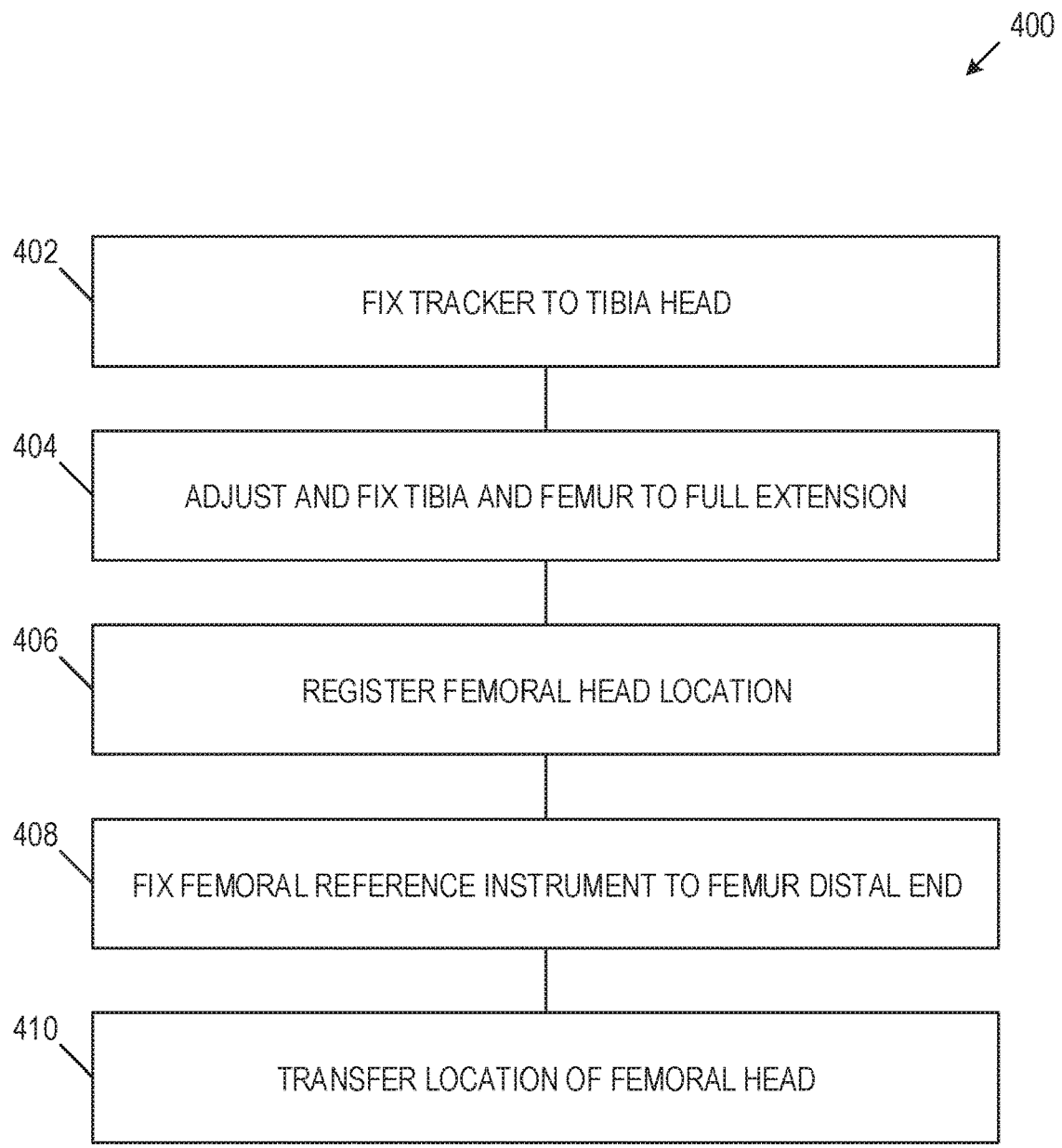
FIG. 4 illustrates an example technique for computer-assisted identification of femoral head, in accordance with some embodiments.

FIG. 4 illustrates an example technique 400 for computer-assisted identification of femoral head. Technique 400 may provide important information for recreating proper kinematic alignment, such as in a partial or total knee arthroplasty procedure. One benefit for the technique described here is the ability to find the location of the femoral head without requiring tracking of the femur, thereby avoiding the need to attach a tracking frame to the femur. In this example, technique 400 can include operations such as fixing a tracking device to the tibia 402, adjusting and fixing the leg into full extension 404, registering the location of the femoral head 406, fixing a tracking device to the distal end of the femur 408, and transferring the location of the femoral head 410. In this example, technique 400 begins with fixing a tracking device to the tibia 402.

The tracking device may be fixed to various locations on the tibia, provided that the tracking device is fixed to a single location on the tibia. At 404, technique 400 can continue by adjusting and fixing the leg into full extension 404. The leg may be fixed by adjusting the leg into full extension and fixing the relative locations of the femur and the tibia, such as by using braces, an exoskeleton, or by a surgeon holding the femur and tibia in extension during the following operations to register the location of the femoral head. In various examples, the femur and tibia can be held in extension by braces or exoskeleton type devices. At 406, technique 400 can continue by registering the location of the femoral head, such as by tracking movement of the leg in extension with the tracking device on the tibia. By digitizing points from the tracker on the tibia, the location of the center of the femoral head can be calculated, such as by assuming that the center of the femoral head is at the center of the point of rotation of the collected points. When the leg is extension, the entire leg can be moved into different positions in space, and similar steps can be used to locate the femoral head. Following registering the femoral head location 406, technique 400 may continue with operations that include tracking referencing the tracker on the tibia, such as when the tracking device provides sufficient information about the positions of the relevant bones. In various examples, the distal end of the femur may need to be tracked for further operations, such as resections to be performed on the distal end of the femur. In such examples, technique 400 may further include fixing a tracking device to the distal end of the femur 408. Technique 400 may further include transferring the location of the femoral head 410. For example, the femoral head location may be transferred from being relative to the tracking device on the tibia to being referenced from the new tracking device on the femur.

Figure 5:
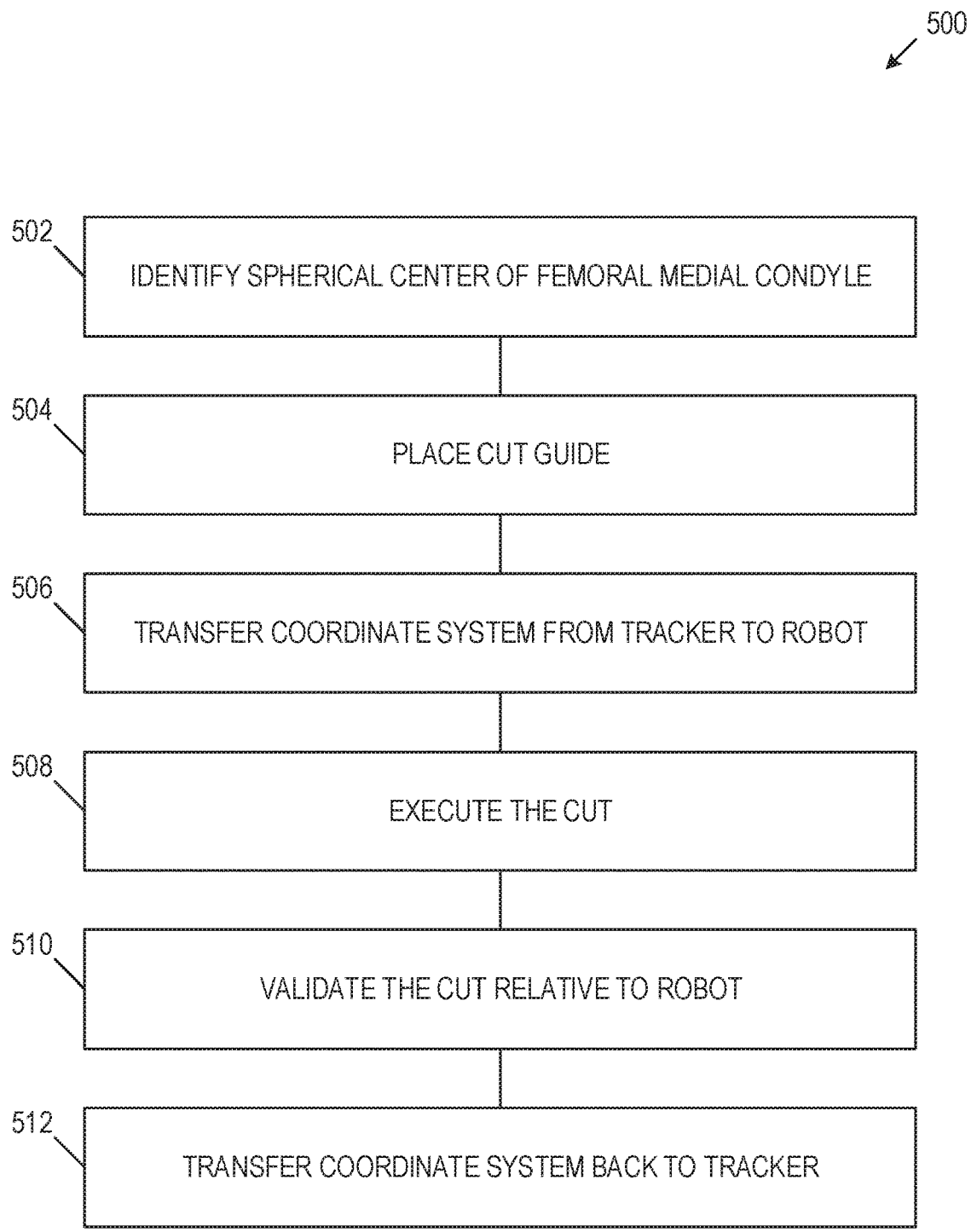
FIG. 5 illustrates a second technique for femoral medial condyle spherical center tracking, in accordance with some embodiments.

FIG. 5 illustrates a second technique 500 for femoral medial condyle spherical center tracking, in accordance with some embodiments. Technique 500 uses the spherical center of the medial condyle to share and update the surgical coordinate system during a robotically executed or robotically assisted surgical procedure. Technique 500 includes identification 502 of the spherical center of the medial condyle. As discussed above in reference to FIGS. 3A-3C, identification of the spherical center of the femoral medial condyle can be performed in accordance with various techniques 301A-301C. Additionally, the spherical center may be identified preoperatively or intraoperatively, and may include the attachment of a tracking device at or near the spherical center, such as securing an optical tracking device to a hole drilled into the spherical center. Identification 502 is further described above related to the discussion of workflows. The spherical center location may be tracked within a surgical tracking device, or may be tracked by a robotic surgical device. The spherical center location may be displayed, such as on an augmented reality display. Once the spherical center is identified, a surgical cutting guide may be placed 504 with the surgical location. A robotic surgical device may be used to track the tracking device.

In an example, the robotic surgical device may be in contact with a surgical tracking device, such as an optical tracker, which may be tracked by a camera, or the like. In another example, the location of the robotic surgical device is known relative to the surgical tracking device by attachment of a tracking mechanism. An example robotic surgical device may be the ROSA robotic arm and device from Medtech.

In an example embodiment, a surgical field camera system may include a camera a camera device. A camera device may include a pair of infrared cameras to be a part of a same camera housing as an infrared camera device and placed in fixed positions within the surgical field. For example, the camera device may be an optical tracking system device, such as the Polaris from Northern Digital Inc. (NDI). A tracked object may have one or a plurality of infrared-reflective marker components attached to it, with the infra-red-reflective marker components arranged rigidly in a specified orientation to one another, for example. The plurality of infrared-reflective marker components may be attachable as a rigid structure to a surgical instrument, the robotic surgical device, or an anatomy of a patient.

An optical tracker may be attached to an object for tracking the object in an optical tracking system, in accordance with some examples. The optical tracker may include one or multiple passive reflective fiducial marker components or an active fiducial marker such as a light emitting diode (LED), which may be at a set position on the optical tracker (e.g., relative to one another). The optical tracker may be attached to an object to be detected within the surgical field such as an instrument, a body part (e.g., a bone), or the robotic surgical device. The position and orientation of the object relative to the object tracker may be set and recorded such that an optical tracking system may know the position and orientation of the object by determining the position and orientation of the optical tracker (e.g., using a camera device to capture an image or information about the optical tracker). The position and orientation of the optical tracker may be determined by detecting the one or multiple reflective components and correlating the detected reflective component positioning to the known relative positioning of the multiple reflective components on the optical tracker. In an example, an optical tracker may be the Navitracker from Zimmer Biomet (e.g., using an Orthosoft guidance system).

The coordinates of the spherical center may be transferred 506 from a coordinate system relative to the surgical tracking device to a coordinate system used by a robotic surgical device. In an embodiment, to ensure proper transfer 506 of the coordinates, the location of the robotic surgical device is known relative to the surgical tracking device (e.g., relative to a position of a tracking device statically affixed to a fixed position, such as a base of the robotic surgical device, a surgical table, a camera, a ceiling mounted object, or the like). In an embodiment, the robotic surgical device may be in contact with the surgical tracking device. The robotic surgical device may include a robotically assisted surgical device to assist a surgeon, an autonomous robotic surgical system, or other robotic surgical device. Using the coordinate system of the robotic surgical device, the robotic surgical device may execute 508 a cut, place a cut guide, or perform another surgical procedure or surgical task. Once a cut is completed, one or more features of the cut may be validated 510, where the validation may be performed relative to the coordinate system of the robotic surgical device. In response to the cut validation 510, the robotic surgical device may execute a corrective surgical procedure or may execute subsequent surgical procedures. During a surgical procedure, a patient joint may be moved to adjust a surgical tool, to adjust a camera viewpoint, to test range of motion, or for other surgical purposes. The robotic surgical device may update the coordinate system in response to an adjustment to the patient joint. For example, an adjustment to a hip joint may modify the orientation of a femoral coordinate system, and the robotic surgical device may update the femoral coordinate system orientation in response to the hip joint adjustment. In an embodiment, the robotic surgical device may include an end effector (e.g., end-of-arm tooling) pinned to the femur or other patient location, and the robotic surgical device may detect movement of the end effector and update the coordinate system. Upon completing the surgical procedures, coordinates of the spherical center or another landmark, point of interest, or aspect of an implant may be transferred 512 from the robotic surgical device coordinate system back to the coordinate system of the tracking device. Prior to the transfer 512, additional reference locations may be identified on the bone, where reference locations may be identified using physical location reference markers, using virtual coordinate system locations, or using other identifications. Prior to the transfer 512, the surgical tracking device may be fixed to a location on the bone. For example, the surgical tracking device may be fixed to the hole drilled into the spherical center, or may be fixed to any other location with a position determinable by the robot surgical device.

In an example, the surgical tracking device described herein may be tracked by a camera, such as an infrared camera, or may be tracked by a positioning system, such as a local or global positioning system, for example using an accelerometer or gyroscope to track acceleration or movement, such as from a known starting position. In another example, the surgical tracking device may include a physical connection to a computer or processing device, which may track the location of the surgical tracking device.

The transfer of the coordinate system may allow a surgeon or surgical team member to switch between optimal tracking methodologies during a surgical procedure. For example, an optical system uses an optical tracking device to digitize landmarks and position a cut guide, the coordinate system is transferred to a surgical robot, and the optical tracking device can be removed to allow the surgical robot to execute a surgical procedure without interference by the optical tracking device. In an example, a tracking device is fixed on an articular bony surface prior to a surgical procedure, a surgical procedure is completed to resect a portion of the bony surface, a second tracker is fixed on a newly resected bony surface, and a coordinate system is transferred from the first tracking device coordinate system to the second tracking device coordinate system.

Figure 6:
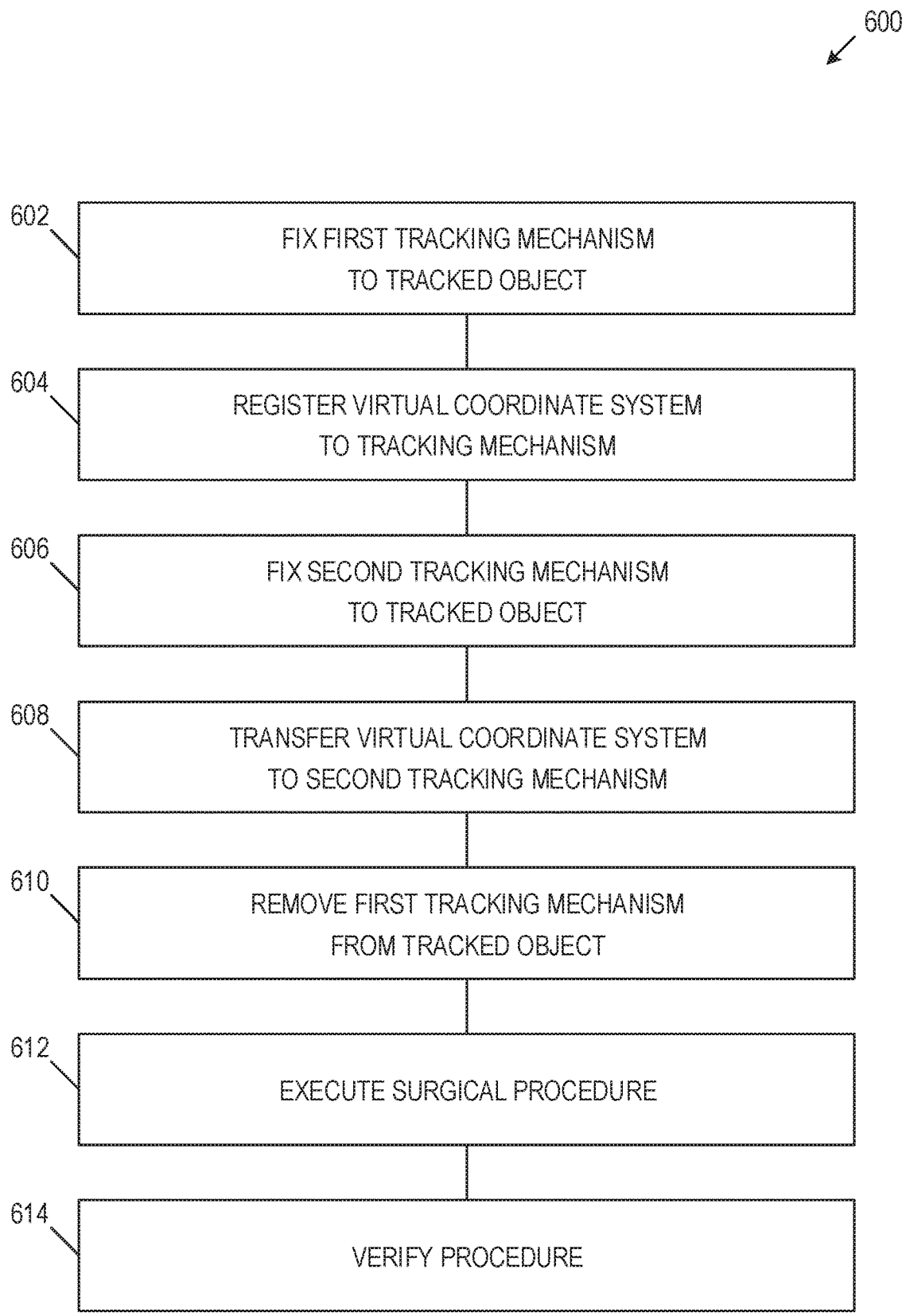
FIG. 6 illustrates a technique showing a coordinate system transfer, in accordance with some embodiments.

FIG. 6 illustrates a technique 600 for a coordinate system transfer, in accordance with some embodiments. In this example, technique 600 includes fixing a first tracking mechanism to a tracked object 602, registering the virtual coordinate system to the tracking mechanism 604, fixing a second tracking mechanism to the tracked object 606, transferring the virtual coordinate system to the second tracking mechanism 608, removing the first tracking mechanism from the tracked object 610, optionally executing a surgical procedure 612, and optionally verifying the surgical procedure 614. Technique 600 may provide the ability to transfer a coordinate system between two tracking mechanism, such as between an optical tracking system and a robotic arm.

At 602, technique 600 begins by fixing a first tracking mechanism to a tracked object. For example, a tracking frame and femur may be fixed together, such as fixing the femur to a tracking table or fixing a three-sphere optical tracking device to the femur. Technique 600 can continue by registering a virtual coordinate system to the first tracking mechanism 604. In an embodiment, registering 604 the virtual coordinate system includes using a calibrated pointer to digitize surface points on the tracked object relative to the tracking frame. At 606, technique 600 can continue by fixing a second tracking mechanism to the tracked object. In the example where the femur is fixed to a tracking table, the second tracking mechanism may include an optical tracking device fixed to the femur. In the example where an optical tracking device is fixed to the femur, the second tracking mechanism may include a robotic arm fixed to the femur. In an example, fixing a robotic arm to the tracked object includes fixing a cut guide to a distal end of a femur, where the cut guide is fixed to the end effector of a robotic arm. Once both the first and second tracking mechanisms are fixed to the tracked object, technique 600 can continue by transferring the previously registered virtual coordinate system to the second tracking mechanism 608. For example, a robotic arm tracking mechanism is able to track the location of the end effector in three-dimensional space, but initially does not inherently have knowledge of the location of the femur in the reference frame of the optical tracking device. With the robotic arm fixed to the femur, such as via the cut guide fixed to the end effector, the virtual coordinate system and all known locations (e.g., location of the femoral head and/or location and orientation of surface points on a condyle of the femur) can be transferred to the robotic arm. In an example, a pre-operative resection plan can be virtually aligned with a femur using the first tracking mechanism, then when the robotic arm with a cut guide is fixed to the femur the pre-operative resection plan can be transferred along with the virtual coordinate system to the robotic arm controlling the cut guide. Following coordinate system transfer, technique 600 continues by removing the first tracking mechanism from the tracked object 610, such as removing an optical tracking mechanism from a femur. For example, while a tracking mechanism attached to a bore (e.g., bore 212) may be used to identify a medial condyle spherical center, the same tracking mechanism attached to the bore may interfere with resections or other procedures. By transferring the coordinate system to a secondary tracking mechanism (e.g., a robotic arm), the bore-mounted tracking mechanism may be removed to execute a resection or other procedure, and the bore-mounted tracking mechanism may be reattached and the coordinate system transferred back following the resection. At 612, technique 600 can optionally continue by executing a surgical procedure, such as resecting a femoral condyle. At 614, technique 600 can optionally continue by verifying the surgical procedure. In an example, verifying the surgical procedure can involve transferring the virtual coordinate system back to the first tracking mechanism (e.g., surgical tool 208 tracking the spherical center of the medial condyle) to verify resections relative to the spherical center.

In a resecting example, securing the first tracking mechanism 602 includes drilling a hole into the spherical center of the femoral medial condyle and inserting an optical tracking pin that is aligned with the spherical center of the femoral medial condyle. To facilitate reinsertion of an optical tracker, the shape of the hole may include a cross-section that provides a predetermined optical tracker orientation, such as including a cross-section that can only be inserted in a particular orientation. The optical tracking pin may be registered 604, and a cut guide may be attached to the femoral condyle. A surgical robot effector may be attached to the femur 606, and the coordinate system may be transferred to the surgical robot 608. The surgical tracking pin may be removed from the femur, and a surgical procedure may be executed 612, such as resecting the femoral condyle.

Following resecting the condyle, verifying the surgical procedure 614 may include inserting an optical tracker in the remaining hole (e.g., the non-resected portion of the hole) to verify the motion of the femur or the surface of the femoral condyle. The transfer of the virtual coordinate system from the robotic arm controlling the cut guide to the optical tracker can accommodate any point on the femur with a position identifiable by contact with the robot arm. For example, when verifying the surgical procedure 614, an optical tracker may be attached at the non-resected portion of the hole, or may be attached at other locations on the femur. Similarly, the optical tracker may be attached at the point of contact between the robotic arm and the femur, which may or may not be the same point at which the first tracking mechanism was fixed to the femur at 602.

Figure 7:
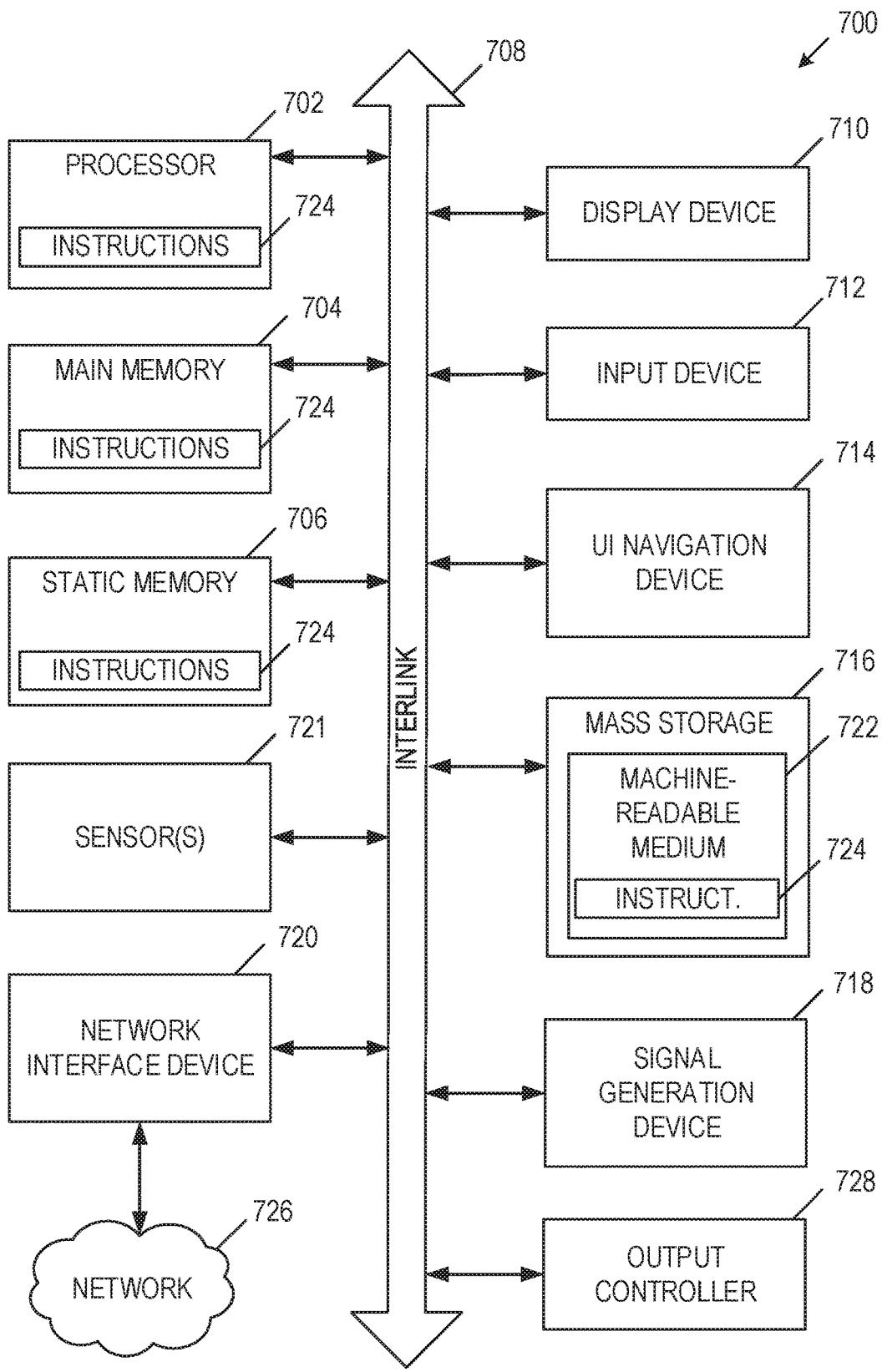
FIG. 7 illustrates generally an example of a block diagram of a machine upon which any one or more of the techniques (e.g., methodologies) discussed herein may perform in accordance with some embodiments.

FIG. 7 illustrates generally an example of a block diagram of a machine 700 upon which any one or more of the techniques (e.g., methodologies) discussed herein may perform in accordance with some embodiments. In alternative embodiments, the machine 700 may operate as a standalone device or may be connected (e.g., networked) to other machines. In a networked deployment, the machine 700 may operate in the capacity of a server machine, a client machine, or both in server-client network environments. The machine 700 may be a personal computer (PC), a tablet PC, a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate on, logic or a number of components, modules, or like mechanisms. Such mechanisms are tangible entities (e.g., hardware) capable of performing specified operations when operating. In an example, the hardware may be specifically configured to carry out a specific operation (e.g., hardwired). In an example, the hardware may include configurable execution units (e.g., transistors, circuits, etc.) and a computer readable medium containing instructions, where the instructions configure the execution units to carry out a specific operation when in operation. The configuring may occur under the direction of the executions units or a loading mechanism. Accordingly, the execution units are communicatively coupled to the computer readable medium when the device is operating. For example, under operation, the execution units may be configured by a first set of instructions to implement a first set of features at one point in time and reconfigured by a second set of instructions to implement a second set of features.

Machine (e.g., computer system) 700 may include a hardware processor 702 (e.g., a central processing unit (CPU), a graphics processing unit (GPU), a hardware processor core, or any combination thereof), a main memory 704 and a static memory 706, some or all of which may communicate with each other via an interlink (e.g., bus) 708. The machine 700 may further include a display unit 710, an alphanumeric input device 712 (e.g., a keyboard), and a user interface (UI) navigation device 714 (e.g., a mouse). In an example, the display unit 710, alphanumeric input device 712 and UI navigation device 714 may be a touch screen display. The display unit 710 may include goggles, glasses, or other AR or VR display components. For example, the display unit may be worn on a head of a user and may provide a heads-up-display to the user. The alphanumeric input device 712 may include a virtual keyboard (e.g., a keyboard displayed virtually in a VR or AR setting).

The machine 700 may additionally include a storage device (e.g., drive unit) 716, a signal generation device 718 (e.g., a speaker), a network interface device 720, and one or more sensors 721, such as a global positioning system (GPS) sensor, compass, accelerometer, or other sensor. The machine 700 may include an output controller 728, such as a serial (e.g., universal serial bus (USB), parallel, or other wired or wireless (e.g., infrared (IR), near field communication (NFC), etc.) connection to communicate or control one or more peripheral devices.

The storage device 716 may include a machine-readable medium 722 that is non-transitory on which is stored one or more sets of data structures or instructions 724 (e.g., software) embodying or utilized by any one or more of the techniques or functions described herein. The instructions 724 may also reside, completely or at least partially, within the main memory 704, within static memory 706, or within the hardware processor 702 during execution thereof by the machine 700. In an example, one or any combination of the hardware processor 702, the main memory 704, the static memory 706, or the storage device 716 may constitute machine-readable media.

While the machine-readable medium 722 is illustrated as a single medium, the term "machine readable medium" may include a single medium or multiple media (e.g., a centralized or distributed database, or associated caches and servers) configured to store the one or more instructions 724.

The term "machine readable medium" may include any medium that is capable of storing, encoding, or carrying instructions for execution by the machine 700 and that cause the machine 700 to perform any one or more of the techniques of the present disclosure, or that is capable of storing, encoding or carrying data structures used by or associated with such instructions. Non-limiting machine-readable medium examples may include solid-state memories, and optical and magnetic media. Specific examples of machine-readable media may include non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 724 may further be transmitted or received over a communications network 726 using a transmission medium via the network interface device 720 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, as the personal area network family of standards known as Bluetooth® that are promulgated by the Bluetooth Special Interest Group, peer-to-peer (P2P) networks, among others. In an example, the network interface device 720 may include one or more physical jacks (e.g., Ethernet, coaxial, or phone jacks) or one or more antennas to connect to the communications network 726. In an example, the network interface device 720 may include a plurality of antennas to communicate wirelessly using at least one of single-input multiple-output (SIMO), multiple-input multiple-output (MIMO), or multiple-input single-output (MISO) techniques. The term "transmission medium" shall be taken to include any intangible medium that is capable of storing, encoding, or carrying instructions for execution by the machine 700, and includes digital or analog communications signals or other intangible medium to facilitate communication of such software.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or other code. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and other media.

What is claimed is:

1. A femoral medial condyle spherical center tracking method comprising:
   identifying, using an arm of a robotic surgical device, a plurality of tibial-femoral contact points between a femur and a tibia;
   digitizing a femoral medial condyle based on the plurality of tibial-femoral contact points;
   intraoperatively identifying coordinates of a spherical center of the femoral medial condyle at a processor of the robotic surgical device based on the digitized femoral medial condyle, wherein identifying the coordinates of the spherical center includes:
   inserting a pin in a femoral intramedullary canal;
   applying a line down a center of a surface of the femoral medial condyle;
   securing a spherical center guide to the pin; and
   rotating the spherical center guide based on the applied line to identify a spherical center external location and a spherical center depth; and
   executing a surgical procedure relative to the spherical center.

2. The method of claim 1, wherein identifying the spherical center includes:
   determining a joint line distance from the femoral medial condyle to a distal and posterior joint line; and
   determining a posterior aspect radius of the femoral medial condyle, wherein identifying the coordinates of the spherical center is based on the posterior aspect radius.

3. The method of claim 1, wherein identifying the coordinates of the spherical center includes immobilizing the femur based on a femur fixation device.

4. The method of claim 3, wherein determining the spherical center includes:
   fitting a virtual sphere to the digitized points; and
   locating the center of the virtual sphere.

5. The method of claim 3, wherein determining the spherical center includes:
   locating a mid-line of the femoral medial condyle;
   determining a mid-line plane using mechanical axis information; and
   fitting a circle to the digitized points on the mid-line plane.

6. The method of claim 1, wherein identifying the spherical center includes identifying a femoral head location of a femur.

7. The method of claim 1, wherein identifying the spherical center includes identifying a femoral head location of the femur by registering the femoral head location using a tracking device when the tibia and the femur are in full extension.

8. The method of claim 7, further comprising:
   fixing a femoral reference instrument to a femoral distal end; and
   transferring the femoral head location to a femoral head-tracking device.

9. A robotic surgical device for tracking a femoral medial condyle spherical center comprising:
   a robotic controller to autonomously manipulate a robotic arm to identify a plurality of tibial-femoral contact points between a femur and a tibia; and
   a processor to:
   digitize a femoral medial condyle based on the plurality of tibial-femoral contact points;
   intraoperatively identify coordinates of a spherical center of the femoral medial condyle at a processor of the robotic surgical device based on the digitized femoral medial condyle; and
   control the robotic arm to cause a portion of a surgical procedure to be executed relative to the spherical center;
   wherein to identify the coordinates of the spherical center, the processor is further to:
   digitize a series of points on the femoral medial condyle;
   determine the spherical center of the femoral medial condyle based on the series of points;
   transform coordinates of the spherical center of the femoral medial condyle to a coordinate system based on a femoral reference instrument location and orientation fixed on the distal end of the femur; and
   track the center of the femoral head.

10. The robotic surgical device of claim 9, wherein to identify the coordinates of the spherical center, the processor is further to:
    fit a virtual sphere to the digitized series of points; and
    locate the center of the virtual sphere.

11. The robotic surgical device of claim 9, wherein to identify the coordinates of the spherical center, the processor is further to:
    locate a mid-line of the medial femoral medial condyle;
    determine a mid-line plane using mechanical axis information; and
    fit a circle to the digitized points on the mid-line plane.

12. The robotic surgical device of claim 9, wherein to identify the coordinates of the spherical center, the processor is further to:
    determine a tibial flexion-extension axis;
    determine a plurality of tibial tracking points within a virtual coordinate system throughout a tibial adjustment based on a tracking device fixed to a head of the tibia proximate a femoral head;

digitize a tibial plateau; and identify the plurality of tibial-femoral contact points between the femur and the tibia based on the tibial plateau and the plurality of tibial tracking points.

13. The robotic surgical device of claim 9, wherein to identify the coordinates of the spherical center, the processor is further to:

identify a femoral head location of a femur;

register the femoral head location while the tibia and the femur are fixed in full extension; and transfer the femoral head location to a femoral head tracking device based on a femoral reference instrument fixed to a femoral distal end.

14. A femoral medial condyle spherical center tracking method comprising:

immobilizing a femur based on a femur fixation device;

fixing a tracking device to a head of a tibia proximate a femoral head of the femur;

adjusting the tibia in flexion and extension;

determining a tibial flexion-extension axis;

determining a plurality of tibial tracking points within a virtual coordinate system throughout tibial adjustment;

digitizing a tibial plateau;

identifying a plurality of tibial-femoral contact points between the femur and the tibia based on the tibial plateau and the plurality of tibial tracking points;

digitizing a femoral medial condyle of the femur based on the plurality of tibial-femoral contact points;

intraoperatively identifying coordinates of a spherical center of the femoral medial condyle at a processor of a robotic surgical device based on the digitized femoral medial condyle; and outputting the coordinates of a spherical center for use in a surgical procedure.

15. The method of claim 14, wherein intraoperatively identifying coordinates of the spherical center includes identifying the femoral head location of the femur by registering the femoral head location using a tracking device when the tibia and the femur are in full extension.

16. The method of claim 15, further comprising:

fixing a femoral reference instrument to a femoral distal end; and transferring the femoral head location to a femoral head-tracking device.

17. A robotic surgical device for tracking a femoral medial condyle spherical center comprising:

a robotic controller to autonomously manipulate a robotic arm to identify a plurality of tibial-femoral contact points between a femur and a tibia; and a processor to:

digitize a femoral medial condyle based on the plurality of tibial-femoral contact points; and intraoperatively identify coordinates of a spherical center of the femoral medial condyle at a processor of the robotic surgical device based on the digitized femoral medial condyle;

wherein to identify the coordinates of the spherical center, the robotic arm is controlled by the robotic controller to:

insert a pin in a femoral intramedullary canal;

secure a spherical center guide to the pin; and rotate the spherical center guide based on a line down a center of a surface of the femoral medial condyle to identify a spherical center external location and a spherical center depth; and control the robotic arm to cause a portion of a surgical procedure to be executed relative to the spherical center.

18. The robotic surgical device of claim 17, wherein to identify the coordinates of the spherical center, the processor is further to:

determine a joint line distance from the femoral medial condyle to a distal and posterior joint line; and determine a posterior aspect radius of the femoral medial condyle, wherein identifying coordinates of the spherical center is based on the posterior aspect radius.

* * * * *